United States Patent
Ari D'Agostino et al.

(10) Patent No.: US 10,945,975 B2
(45) Date of Patent: Mar. 16, 2021

(54) DELAYING LATENCY TO SEIZURE BY COMBINATIONS OF KETONE SUPPLEMENTS

(71) Applicant: UNIVERSITY OF SOUTH FLORIDA, Tampa, FL (US)

(72) Inventors: Csilla Ari D'Agostino, Tampa, FL (US); Dominic Paul D'Agostino, Tampa, FL (US); Jay B. Dean, Land O'Lakes, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/344,379

(22) PCT Filed: Oct. 24, 2017

(86) PCT No.: PCT/US2017/058083
§ 371 (c)(1),
(2) Date: Apr. 24, 2019

(87) PCT Pub. No.: WO2018/081118
PCT Pub. Date: May 3, 2018

(65) Prior Publication Data
US 2019/0255003 A1    Aug. 22, 2019

Related U.S. Application Data

(60) Provisional application No. 62/411,754, filed on Oct. 24, 2016.

(51) Int. Cl.
*A61K 31/191* (2006.01)
*A61P 25/08* (2006.01)
(Continued)

(52) U.S. Cl.
CPC ............ *A61K 31/191* (2013.01); *A61K 31/19* (2013.01); *A61K 31/20* (2013.01); *A61K 31/225* (2013.01);
(Continued)

(58) Field of Classification Search
CPC .... A61K 31/191; A61K 31/225; A61K 31/20; A61K 31/19; A61P 25/08
See application file for complete search history.

(56) References Cited

U.S. PATENT DOCUMENTS 8,124,589 B2 * 2/2012 Henderson ................ A23L 2/52
514/23
2010/0316733 A1   12/2010 Locklear
(Continued)

FOREIGN PATENT DOCUMENTS

EP    2316530    8/2014
WO    00/28985 A1    5/2000
(Continued)

OTHER PUBLICATIONS

American Cancer Society, Treating Advanced Cancer. http://www.cancer.org/treatment/understanding-your-diagnosis/advanced-cancer/treatment.html Accessed on Oct. 4, 2017.
(Continued)

*Primary Examiner* — San Ming R Hui
(74) *Attorney, Agent, or Firm* — Meunier Carlin & Curfman LLC

(57) ABSTRACT

Provided herein are compositions and methods for preventing central nervous system oxygen toxicity in a subject.

20 Claims, 7 Drawing Sheets

(51) Int. Cl.
| | |
|---|---|
| A61K 31/19 | (2006.01) |
| A61K 31/225 | (2006.01) |
| A61K 31/20 | (2006.01) |
| A61K 33/14 | (2006.01) |
| A61P 39/00 | (2006.01) |
| A61P 25/00 | (2006.01) |

(52) U.S. Cl.
CPC .............. *A61K 33/14* (2013.01); *A61P 25/00* (2018.01); *A61P 25/08* (2018.01); *A61P 39/00* (2018.01); *A61K 2300/00* (2013.01)

(56) References Cited

U.S. PATENT DOCUMENTS

| | | |
|---|---|---|
| 2013/0289116 A1 | 10/2013 | Martin et al. |
| 2014/0072654 A1 | 3/2014 | D'Agostino et al. |
| 2014/0073693 A1 | 3/2014 | D'Agostino et al. |
| 2014/0350105 A1 | 11/2014 | D'Agostino et al. |

FOREIGN PATENT DOCUMENTS

| | | |
|---|---|---|
| WO | 02062327 | 8/2002 |
| WO | 2012113572 | 8/2012 |
| WO | 2015156865 | 10/2015 |

OTHER PUBLICATIONS

American Cancer Society, Understanding Advanced Cancer, Metastatic Cancer, and Bone Metastasis. What is advanced cancer? http://www.cancer.org/treatment/understanding-your-diagnosis/advanced-cancer/what-is.html Accessed on Oct. 4, 2017.
Aykin-Burns, N., et al. Increased levels of superoxide and hydrogen peroxide mediate the differential susceptibility of cancer cells vs. Normal cells to glucose deprivation. Biochem J 418 (2009): 29-37.
Bennett, et al. (2008) Hyperbaric oxygenation for tumour sensitisation to radiotherapy: a systematic review of randomised controlled trials. Cancer treatment reviews 34: 577-591.
Bitterman, et al., Starvation and dehydration attenuate CNS oxygen toxicity in rats. Brain research 761.1 (1997): 146-150.
Bitterman, et al., The effect of sodium phenytoin on central nervous system oxygen toxicity. Aviation, space, and environmental medicine 58.3 (1987): 224-226.
Bitterman, N., et al., Beta-carotene and CNS oxygen toxicity in rats. Journal of applied physiology 76.3 (1994): 1073-1076.
Bough, Kristopher J., and Jong M. Rho. Anticonvulsant mechanisms of the ketogenic diet. Epilepsia 48.1 (2007): 43-58.
Brian, Johnny E. Current Thoughts on Mechanisms of Hyperoxic Seizures. https://pdfs.semanticscholar.org/254c/7b314a304530044a07a09af7976dd5f0273b.pdf, last accessed Jun. 12, 2017, 24 pages.
Brunengraber, Henri. Potential of ketone body esters for parenteral and oral nutrition. Nutrition13.3 (1997): 233-235.
Cahill Jr, George F. Fuel metabolism in starvation Annu. Rev. Nutr. 26 (2006): 1-22.
Chavko, et al., Effect of MK-801 on seizures induced by exposure to hyperbaric oxygen: comparison with AP-7. Toxicology and applied pharmacology 151.2 (1998): 222-228.
Chavko, et al., Relationship between protein nitration and oxidation and development of hyperoxic seizures. Nitric Oxide vol. 9, Issue 1, (Aug. 2003): 18-23.
Chavko, M., et al., Attenuation of Brain Hyperbaric Oxygen Toxicity of Fasting is Not Related to Ketosis. Undersea Hyperb Med. 1999 Summer;26(2):99-103.
Ciraolo, Susan T., et al. Model of extreme hypoglycemia in dogs made ketotic with (R, S)-1, 3-butanediol acetoacetate esters. American Journal of Physiology-Endocrinology and Metabolism 269.1 (1995): E67-E75.
Clark, et al., Toxicity of Oxygen, Carbon Dioxide, and Carbon Monoxide. (1997): 131-145.
Cox, Pete J., et al. Nutritional ketosis alters fuel preference and thereby endurance performance in athletes. Cell metabolism 24.2 (2016): 256-268.
Cuezva, et al., The bioenergetic signature of cancer: a marker of tumor progression. Cancer research 62 (2002): 6674-6681.
D'Agostino, et al., Therapeutic ketosis with ketone ester delays central nervous system oxygen toxicity seizures in rats, Am J Physiol Regul Integr Comp Physiol 304 (2013) R829-R836.
D'Agostino, Dominic P., et al., Superoxide ($\cdot O_2-$) production in CA1 neurons of rat hippocampal slices exposed to graded levels of oxygen. Journal of neurophysiology 98.2 (2007): 1030-1041.
D'Agostino, et al., Acute hyperoxia increases lipid peroxidation and induces plasma membrane blebbing in human U87 glioblastoma cells. Neuroscience 159 (2009): 1011-1033.
Daruwalla, Jurstine, and Chris Christophi. Hyperbaric oxygen therapy for malignancy: a review. World journal of surgery 30.12 (2006): 2112-2131.Abstract.
Demchenko, Ivan T., et al. Oxygen seizure latency and peroxynitrite formation in mice lacking neuronal or endothelial nitric oxide synthases. Neuroscience letters 344.1 (2003): 53-56.
Desrochers, et al. Metabolism of (R, S)-1, 3-butanediol acetoacetate esters, potential parenteral and enteral nutrients in conscious pigs. American Journal of Physiology-Endocrinology and Metabolism 268.4 (1995): E660-E667.
Fearon, K. C., et al. Cancer cachexia: influence of systemic ketosis on substrate levels and nitrogen metabolism. The American journal of clinical nutrition 47.1 (1988): 42-48.
Fidler, Isaiah J. Tumor heterogeneity and the biology of cancer invasion and metastasis. Cancer research 38.9 (1978): 2651-2660.
Fife, C. M., J. A. McCarroll, and M. Kavallaris. Movers and shakers: cell cytoskeleton in cancer metastasis. British journal of pharmacology171.24 (2014): 5507-5523.
Fine, Eugene J., et al. Acetoacetate reduces growth and ATP concentration in cancer cell lines which over-express uncoupling protein 2. Cancer cell international 9.1 (2009): 14.
Freeman, John M., and Eric H. Kossoff. Ketosis and the ketogenic diet, 2010: advances in treating epilepsy and other disorders. Advances in pediatrics 57.1 (2010): 315-329.
Garcia III, et al., Hyperbaric hyperoxia and normobaric reoxygenation increase excitability and activate oxygen-induced potentiation in CA1 hippocampal neurons. Journal of applied physiology 109.3 (2010): 804-819.
Gasior, Maciej, et al. The anticonvulsant activity of acetone, the major ketone body in the ketogenic diet, is not dependent on its metabolites acetol, 1, 2-propanediol, methylglyoxal, or pyruvic acid. Epilepsia 48.4 (2007): 793-800.
Gerschman, Rebeca. Oxygen poisoning and x-irradiation: a mechanism in common. Science. May 7, 1954;119(3097):623-6.
Gill & Bell (2004) Hyperbaric oxygen: its uses, mechanisms of action and outcomes. QJM 97.
Gillies, Robert J., Ian Robey, and Robert A. Gatenby. Causes and consequences of increased glucose metabolism of cancers. Journal of Nuclear Medicine 49.2 (2008): 24S-42S.
Greene, Amanda E., et al., Perspectives on the metabolic management of epilepsy through dietary reduction of glucose and elevation of ketone bodies. Journal of neurochemistry 86.3 (2003): 529-537.
Habib, et al., Ethane production rate in vivo is reduced with dietary restriction. Journal of Applied Physiology 68.6 (1990): 2588-2590.
Henderson, Samuel T. Ketone bodies as a therapeutic for Alzheimer's disease. Neurotherapeutics 5.3 (2008): 470-480.
Hoogsteen, et al., The hypoxic tumour microenvironment, patient selection and hypoxia-modifying treatments. Clinical oncology (Royal College of Radiologists (Great Britain)) 19 (2007): 385-396. https://www.mayocliniclabs.com/test-catalog/Clinical+and+Interpretive/9251, last accessed Mar. 13, 2017.
Hursting, et al., Calories and carcinogenesis: lessons learned from 30 years of calorie restriction research. Carcinogenesis 31 (2010): 83-89.
Isidoro, Antonio, et al. Alteration of the bioenergetic phenotype of mitochondria is a hallmark of breast, gastric, lung and oesophageal cancer. Biochemical Journal 378.1 (2004): 17-20.

(56) References Cited

OTHER PUBLICATIONS

John (2001) Dysfunctional mitochondria, not oxygen insufficiency, cause cancer cells to produce inordinate amounts of lactic acid: the impact of this on the treatment of cancer. Medical hypotheses 57: 429-460.
Juge, Narinobu, et al. Metabolic control of vesicular glutamate transport and release. Neuron68.1 (2010): 99-112.
Katyal, et al. (2000) The ketogenic diet in refractory epilepsy: the experience of Children's Hospital of Pittsburgh. Clinical pediatrics 39: 153-159.
Kesl, Shannon L., et al. Effects of exogenous ketone supplementation on blood ketone, glucose, triglyceride, and lipoprotein levels in Sprague—Dawley rats. Nutrition & metabolism 13.1 (2016): 9.
Kim, Do Young, et al., Ketones prevent synaptic dysfunction induced by mitochondrial respiratory complex inhibitors. Journal of neurochemistry 114.1 (2010): 130-141. p. 137, col. 1.
Klein, Pavel, et al. Ketogenic diet treatment in adults with refractory epilepsy. Epilepsy & Behavior 19.4 (2010): 575-579.
Klement & Kammerer (2011) Is there a role for carbohydrate restriction in the treatment and prevention of cancer? Nutrition & metabolism 8: 75.
Kossoff, Eric H. et al. The Ketogenic and Modified Alkins Diets, 2016, pp. 12-13. Printed in the United States of America by McNaughton & Gunn.
Le O-T, Denko N, Giaccia A (2004) Hypoxic gene expression and metastasis. Cancer metastasis reviews 23: 293-310.
Liberti, Maria V., et al., The Warburg effect: how does it benefit cancer cells? Trends in biochemical sciences 41.3 (2016): 211-218.
Likhodii, Sergei S., et al. Anticonvulsant properties of acetone, a brain ketone elevated by the ketogenic diet. Annals of neurology 54.2 (2003): 219-226.
Likhodii, Sergei S., et al., Acetone as an anticonvulsant. Epilepsia 49 (2008): 83-86.
Lin, Yiguang, and Dana Jamieson. Effects of antioxidants on oxygen toxicity in vivo and lipid peroxidation in vitro. Pharmacology & toxicology70.4 (1992): 271-277.
Lo E.H. et al., Mechanisms, challenges and opportunities in stroke. Nat Rev Neurosci. (May 2003), 4(5):399-415.
Heiden, et al., (2011) Aerobic glycolysis: meeting the metabolic requirements of cell proliferation. Annual review of cell and developmental biology 27: 441-464.
Miceli, et al., Common and Cell Type-Specific responses of human cells to mitochondrial dysfunction. Experimental Cell Research, vol. 302, (2005), pp. 270-280.
Maalouf, Marwan, et al. Ketones inhibit mitochondrial production of reactive oxygen species production following glutamate excitotoxicity by increasing NADH oxidation. Neuroscience 145.1 (2007): 256-264.
Maalouf, Marwan, et al., The neuroprotective properties of calorie restriction, the ketogenic diet, and ketone bodies. Brain research reviews 59.2 (2009): 293-315.
Magee, et al., The inhibition of malignant cell growth by ketone bodies. The Australian journal of experimental biology and medical science, 57 (1979): 529-539.
Masko, et al., Low-carbohydrate diets and prostate cancer: how low is "low enough"? Cancer prevention research (Philadelphia, Pa) (2010) 3: 1124-1131.
Maurer, Gabriele D., et al. Differential utilization of ketone bodies by neurons and glioma cell lines: a rationale for ketogenic diet as experimental glioma therapy. BMC cancer 11.1 (2011): 315.
Mavropoulos, John C., et al. "Is there a role for a low-carbohydrate ketogenic diet in the management of prostate cancer?" Urology 68.1 (2006): 15-18.
Mavropoulos, John C., et al. "The effects of varying dietary carbohydrate and fat content on survival in a murine LNCaP prostate cancer xenograft model." Cancer prevention research 2.6 (2009): 557-565.
McNally, Melanie A., and Adam L. Hartman. Ketone bodies in epilepsy. Journal of neurochemistry 121.1 (2012): 28-35.

Medina Glutamine and cancer. The Journal of nutrition 131: 2539S-2542S; discussion (2001): 2550S-2531S.
Milder, Julie B., Li-Ping Liang, and Manisha Patel. Acute oxidative stress and systemic Nrf2 activation by the ketogenic diet. Neurobiology of disease 40.1 (2010): 238-244.
Moen, Ingrid, and Linda EB Stuhr. "Hyperbaric oxygen therapy and cancer—a review." Targeted oncology 7.4 (2012): 233-242.
Moen, Ingrid, et al. "Hyperoxic treatment induces mesenchymal-to-epithelial transition in a rat adenocarcinoma model." PloS one 4.7 (2009): e6381, 8 pages.
Mukherjee, et al., Energy intake and prostate tumor growth, angiogenesis, and vascular endothelial growth factor expression. Journal of the National Cancer Institute (1999) 91: 512-523.
Mukherjee, et al. "Dietary restriction reduces angiogenesis and growth in an orthotopic mouse brain tumour model." British journal of cancer86.10 (2002): 1615-1621.
National Cancer Institute Metastatic Cancer. What is Metastatic Cancer? https://www.cancer.gov/typers/metastatic-cancer Accessed on Oct. 4, 2017.
Nebeling, Linda C., and Edith Lerner. "Implementing a ketogenic diet based on medium-chain triglyceride oil in pediatric patients with cancer." Journal of the American Dietetic Association 95.6 (1995): 693-697.
Neidle, Stephen, Cancer Drug Design and Discovery Neidle, Stephen, ed. (Elsevier/Academic Press, 2008) pp. 427-431.
Otto, Christoph, et al. "Growth of human gastric cancer cells in nude mice is delayed by a ketogenic diet supplemented with omega-3 fatty acids and medium-chain triglycerides." BMC cancer 8.1 (2008): 122.
Oudard, et al., Gliomas are driven by glycolysis: putative roles of hexokinase, oxidative phosphorylation and mitochondrial ultrastructure. Anticancer research (1997) 17: 1903-1911.
Petre, et al., Hyperbaric oxygen as a chemotherapy adjuvant in the treatment of metastatic lung tumors in a rat model. The Journal of thoracic and cardiovascular surgery 125 (2003): 85.
Puchowicz, Michelle A., et al. Dog model of therapeutic ketosis induced by oral administration of R, S-1, 3-butanediol diacetoacetate. The Journal of nutritional biochemistry 11.5 (2000): 281-287.
Poff, et al., The Ketogenic Diet and hyperbaric oxygen therapy prolong survival in mice with systematic metastatic cancer. PLos ONE 2013, e65522.
Raa, et al. Hyperoxia retards growth and induces apoptosis and loss of glands and blood vessels in DMBA-induced rat mammary tumors. BMC cancer 7 (2007): 23.
Rho, Jong M., and Raman Sankar. The ketogenic diet in a pill: is this possible? Epilepsia 49 (2008): 127-133.
Rho, Jong M., et al. Acetoacetate, acetone, and dibenzylamine (a contaminant in L-(+)-β-hydroxybutyrate) exhibit direct anticonvulsant actions in vivo. Epilepsia 43.4 (2002): 358-361.
Rossifanelli, et al., Effect of Energy Substrate Manipulation on Tumor-Cell Proliferation in Parenterally Fed Cancer-Patients. Clinical Nutrition 10 (1991): 228-232.
Sawai, et al., Growth-inhibitory effects of the ketone body, monoacetoacetin, on human gastric cancer cells with succinyl-CoA: 3-oxoacid CoA-transferase (SCOT) deficiency. Anticancer research 24 (2004): 2213-2217.
Schmidt et al., Effects of a ketogenic diet on the quality of life in 16 patients with advanced cancer: A pilot trial. Nutrition & Metabolism 2011, 8:54 Published: Jul. 27, 2011, pp. 1-13 (Year: 2011).
Schumacker, Paul T. Reactive oxygen species in cancer: a dance with the devil. Cancer cell 27.2 (2015): 156-157.
Schumacker, Reactive oxygen species in cancer cells: live by the sword, die by the sword. Cancer cell 10 (2006): 175-181.
Seyfried & Shelton, Cancer as a metabolic disease. Nutrition & metabolism 7 (2010): 7.
Seyfried, et al., Role of glucose and ketone bodies in the metabolic control of experimental brain cancer. British journal of cancer 89 (2003): 1375-1457.
Seyfried, et al., Targeting energy metabolism in brain cancer through calorie restriction and the ketogenic diet. Journal of cancer research and therapeutics 5 Suppl 1 (2009): 15.

(56) References Cited

OTHER PUBLICATIONS

Seyfried, et al., Targeting energy metabolism in brain cancer with calorically restricted ketogenic diets. Epilepsia 49 Suppl 8 (2008): 114-116.

Skinner, Robert, et al. Ketone bodies inhibit the viability of human neuroblastoma cells. Journal of pediatric surgery 44.1 (2009): 212-216.

Stafford, et al., The ketogenic diet reverses gene expression patterns and reduces reactive oxygen species levels when used as an adjuvant therapy for glioma. Nutrition & metabolism 7 (2010): 74.

Stubbs, Brianna J., et al. On the metabolism of exogenous ketones in humans. Frontiers in physiology 8 (2017): 848.

Stuhr, et al., Hyperbaric oxygen alone or combined with 5-FU attenuates growth of DMBA-induced rat mammary tumors. Cancer letters 210 (2004): 35-40.

Stuhr, et al., Hyperoxia retards growth and induces apoptosis, changes in vascular density and gene expression in transplanted gliomas in nude rats. Journal of neurooncology 85 (2007): 191-202.

Takiguchi, et al., Use of 5-FU plus hyperbaric oxygen for treating malignant tumors: evaluation of antitumor effect and measurement of 5-FU in individual organs. Cancer chemotherapy and pharmacology 47 (2001): 11-14.

Test ID: BYHD. Beta-Hydroxybutyrale, Serum. Mayo Clinic. Mayo Medical Laboratories.

Thompson, et al., Dietary energy restriction in breast cancer prevention. Journal of mammary gland biology and neoplasia 8 (2003): 133-142.

Thompson, et al., Effect of dietary energy restriction on vascular density during mammary carcinogenesis. Cancer research 64 (2004): 5643-5650.

Thompson, et al., Identification of the apoptosis activation cascade induced in mammary carcinomas by energy restriction. Cancer research 64 (2004): 1541-1545.

Tisdale & Brennan, Loss of acetoacetate coenzyme a transferase activity in tumours of peripheral tissues. British journal of cancer 47 (1983): 293-297.

Tisdale & Brennan; A comparison of long-chain triglycerides and medium-chain triglycerides on weight loss and tumor size in a cachexia model. Br. J Cancer (1988), vol. 58, pp. 580-583.

Vaupel & Harrison, Tumor hypoxia: causative factors, compensatory mechanisms, and cellular response. The oncologist 9 Suppl 5 (2004): 4-9.

Vaupel, et al., Treatment resistance of solid tumors: role of hypoxia and anemia. Medical oncology (Northwood, London, England) 18 (2001): 243-259.

Vaupel, et al., Tumor hypoxia and malignant progression. Exp Oncol 2009, 80-86.

Veech, Richard L. The therapeutic implications of ketone bodies: the effects of ketone bodies in pathological conditions: ketosis, ketogenic diet, redox states, insulin resistance, and mitochondrial metabolism. Prostaglandins, leukotrienes and essential fatty acids 70.3 (2004): 309-319.

Vidale, Simone, et al. Postischemic inflammation in acute stroke. Journal of Clinical Neurology 13.1 (2017): 1-9.

Warburg (1956) On respiratory impairment in cancer cells. Science 124: 269-270.

Warburg (1956) On the origin of cancer cells. Science 123: 309-314.

Wheatley, et al., Low-carbohydrate diet versus caloric restriction: effects on weight loss, hormones, and colon tumor growth in obese mice. Nutrition and cancer 60 (2008): 61-68.

Wouters, et al., Targeting hypoxia tolerance in cancer. Drug resistance updates: reviews and commentaries in antimicrobial and anticancer chemotherapy 7 (2004): 25-40.

Wu, et al., Multiparameter metabolic analysis reveals a close link between attenuated mitochondrial bioenergetic function and enhanced glycolysis dependency in human tumor cells. American journal of physiology Cell physiology 292 (2007): C125-136.

Ye, Fang, et al. Efficacy of and patient compliance with a ketogenic diet in adults with intractable epilepsy: a meta-analysis. Journal of Clinical Neurology 11.1 (2015): 26-31.

Yellen, Gary. Ketone bodies, glycolysis, and KATP channels in the mechanism of the ketogenic diet. Epilepsia 49 (2008): 80-82.

Zhou, Weihua, et al. The calorically restricted ketogenic diet, an effective alternative therapy for malignant brain cancer. Nutrition & metabolism 4.1 (2007), 1-15.

Zhu, et al., Effects of dietary energy repletion and Igf-1 infusion on the inhibition of mammary carcinogenesis by dietary energy restriction. Molecular carcinogenesis 42 (2005): 170-176.

Zidan, J., et al. Comparison of HER-2 overexpression in primary breast cancer and metastatic sites and its effect on biological targeting therapy of metastatic disease. British journal of cancer 93.5 (2005): 552-556.

Zuccoli, et al., Metabolic management of glioblastoma multiforme using standard therapy together with a restricted ketogenic diet: Case Report. Nutrition & metabolism 7 (2010): 33.

International Preliminary Report on Patentability for International Application No. PCT/US2012/037099, filing date of May 9, 2012, dated Nov. 12, 2013.

International Preliminary Report on Patentability Opinion issued for Application No. PCT/US2017/058083, dated May 9, 2019.

International Search Report and Written Opinion for International Application No. PCT/US2012/037099, filing date of May 9, 2012, dated Jan. 2, 2013.

International Search Report and Written Opinion issued for Application No. PCT/US2017/058083, dated Jan. 5, 2018.

Extended European Seach Report issued for Application No. 17865919.9, dated Apr. 9, 2020.

Viggiano, Andrea, et al. "Anticonvulsant properties of an oral ketone ester in a pentylenetetrazole-model of seizure." brain research 1618 (2015): 50-54.

* cited by examiner

DELAYING LATENCY TO SEIZURE BY COMBINATIONS OF KETONE SUPPLEMENTS

CROSS-REFERENCE TO RELATED APPLICATION(S)

This application claims priority to U.S. Provisional Application No. 62/411,754, filed on Oct. 24, 2016, which is incorporated fully herein by reference.

STATEMENT OF GOVERNMENT SUPPORT

This invention was made with government support under N00014-07-1-0890 and N00014-16-1-2537 awarded by the Office of Naval Research. The government has certain rights in the invention.

TECHNICAL FIELD

This invention relates to methods of using ketogenic compositions for the prevention of central nervous system (CNS) oxygen toxicity or seizures in a subject.

BACKGROUND

Oxygen toxicity is a condition resulting from the harmful effects of breathing molecular oxygen ($O_2$) at elevated partial pressures resulting in neuronal hyper-excitability and oxidative stress. Hyperbaric oxygen-induced seizures, also known as central nervous system oxygen toxicity (CNS-OT) compromise the safety of undersea divers and patients undergoing hyperbaric oxygen therapy ($HBO_2$ therapy). This condition manifests as tonic-clonic seizures, which carry a significant risk of drowning for divers. CNS-OT occurs with little or no warning and no effective mitigation strategy against it has been identified. As such, methods to treat or prevent CNS-OT are needed.

SUMMARY

Disclosed herein are methods of treating CNS-OT or seizures in a subject. The method may comprise administering a composition comprising a therapeutically effective amount of one or more ketogenic compounds to the subject. The one or more ketogenic compounds may be selected from the group consisting of a ketone ester, a ketone salt, a ketone body precursor, and a combination thereof. The composition may further comprise a medium chain triglyceride. The composition may be administered orally. The subject may be a human.

DETAILED DESCRIPTION

Figure 1:
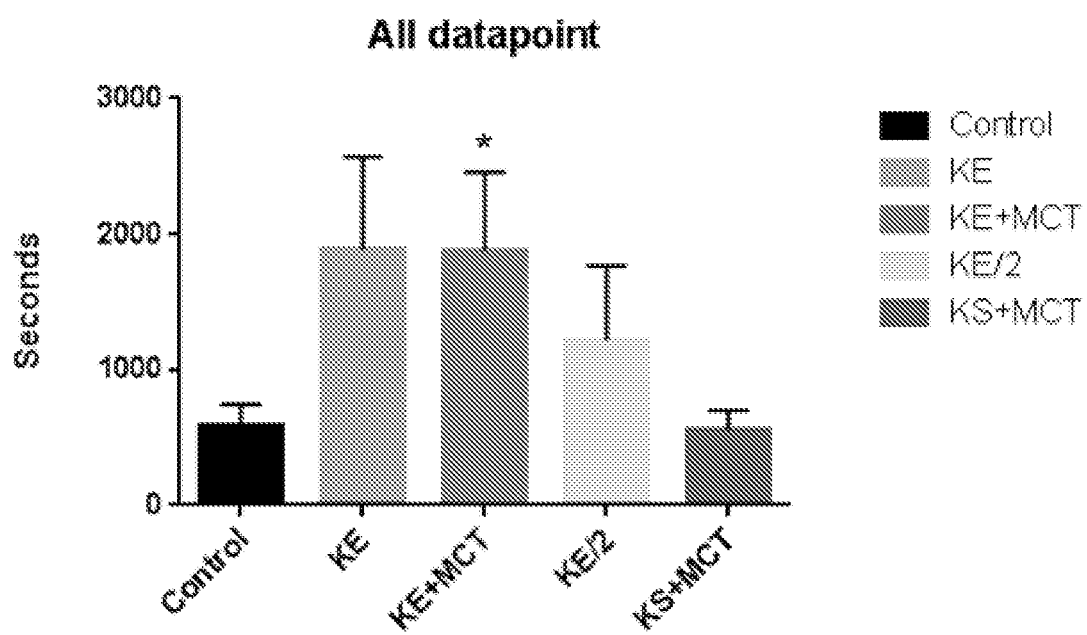
FIGS. 1-3 show latency to time of seizure for all tested rats broken down by treatment regimen.

The present disclosure describes methods of treating CNS-OT or seizures in a subject, comprising administering to the subject a composition comprising one or more ketogenic compounds.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "administration" or "administering" is used throughout the specification to describe the process by which the disclosed ketogenic compositions may be delivered to a subject. Administration will often depend upon the amount of composition administered, the number of doses, and duration of treatment. Multiple doses of the composition may be administered. The frequency and duration of administration of the composition can vary, depending on any of a variety of factors, including patient response, etc. The ketogenic compositions may be administered to the subject by any suitable route. The compositions may be administered orally, parenterally, (including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, and epidural injection) by infusion, by electroporation, or co-administered as a component of any medical device or object to be inserted (temporarily or permanently) into a subject.

The amount of the composition administered can vary according to factors such as the degree of susceptibility of the individual, the age, sex, and weight of the individual, idiosyncratic responses of the individual, the dosimetry, and the like. Detectably effective amounts of the composition of the present disclosure can also vary according to instrument and film-related factors. Optimization of such factors is well within the level of skill in the art.

The term "aliphatic group" is defined as including alkyl, alkenyl, alkynyl, halogenated alkyl and cycloalkyl groups as defined above. A "lower aliphatic group" is an aliphatic group that contains from 1 to 10 carbon atoms.

The term "alkoxy group" is represented by the formula —OR, where R can be an alkyl group, including a lower alkyl group, optionally substituted with an alkenyl, alkynyl, aryl, aralkyl, cycloalkyl, halogenated alkyl, or heterocycloalkyl group, as defined below.

The term "alkenyl group" is defined as a hydrocarbon group of 2 to 24 carbon atoms and structural formula containing at least one carbon-carbon double bond.

The term "alkyl group" is defined as a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkynyl group" is defined as a hydrocarbon group of 2 to 24 carbon atoms and a structural formula containing at least one carbon-carbon triple bond.

The term "aralkyl" is defined as an aryl group having an alkyl group, as defined above, attached to the aryl group. An example of an aralkyl group is a benzyl group.

The term "aryl group" is defined as any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

The terms "beta-hydroxybutyrate,", "βHB", or "BHB" as used interchangeably herein refer to a carboxylic acid having the general formula $CH_3CH_2OHCH_2COOH$. βHB is a ketone body which may be utilized by the body as a fuel source during instances of low glucose levels.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

The term "cycloalkyl group" is defined as a non-aromatic carbon-based ring composed of at least three carbon atoms. Examples of cycloalkyl groups include, but are not limited to, cyclopropyl, cyclobutyl, cyclopentyl, cyclohexyl, etc.

"Derivative" refers to a compound or portion of a compound that is derived from or is theoretically derivable from a parent compound.

The term "ester" as used herein is represented by the formula —OC(O)R, where R can be an alkyl, alkenyl, alkynyl, aryl, aralkyl, cycloalkyl, halogenated alkyl, or heterocycloalkyl group.

"Esterification" refers to the reaction of an alcohol with a carboxylic acid or a carboxylic acid derivative to give an ester.

The term "halogenated alkyl group" is defined as an alkyl group as defined above with one or more hydrogen atoms present on these groups substituted with a halogen (F, Cl, Br, I).

The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "hydroxyl group" is represented by the formula —OH.

The term "ketogenic composition" as used herein refers to a composition comprising one or more ketogenic compounds.

"Ketogenic compound" refers a compound that is capable of elevating ketone body concentrations in a subject.

"Ketone" or "ketone body", as used interchangeably herein, refers to a compound or species which is β-hydroxybutyrate (βHB), acetoacetate, acetone, or a combination thereof. A ketone body may be derived from a ketone body precursor, that is, a compound or species which is a precursor to a ketone body and which may be converted or metabolized to a ketone body in a subject.

"Ketone body ester" or "ketone ester" as used herein, refer to an ester of a ketone body, ketone body precursor, or derivative thereof. Any suitable ketone ester known in the art may be used. For example, the ketone ester may be 1,3 butanediol acetoacetate diester.

"Ketone body salt" or "ketone salt" is a salt of a ketone body, ketone body precursor, or derivative thereof. The ketone salt may be combined with one or more monovalent cations, divalent cations, or alkaline amino acids. Any suitable ketone salt known in the art may be used.

The term "medium chain triglycerides" (MCT) as used herein refers to molecules having a glycerol backbone attached to three medium chain fatty acids. Medium chain fatty acids range from 6 to 12 carbon atoms in length. Exemplary fatty acids are caprylic acid, also known as octanoic acid, comprising 8 carbon molecules, and capric acid, also known as decanoic acid, comprising 10 carbon molecules.

A "pharmaceutically acceptable excipient," "pharmaceutically acceptable diluent," "pharmaceutically acceptable carrier,", "carrier", or "pharmaceutically acceptable adjuvant" as used herein means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use, such as those promulgated by the United States Food and Drug Administration. The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). The subject may be a human or a non-human. The subject or patient may be undergoing other forms of treatment.

The term "treatment", "treat", "treating" or any grammatical variation thereof as used herein, includes but is not limited to, ameliorating or alleviating a symptom of a disease or condition, reducing, preventing, suppressing, inhibiting, lessening, or affecting the progression and/or severity of an undesired physiological change or a diseased condition.

A "therapeutically effective amount," or "effective dosage" or "effective amount" as used interchangeably herein unless otherwise defined, means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. The effective dosage will depend on absorption, distribution, metabolism, and excretion rates of the disclosed exogenous ketones. The dose should be sufficient to affect a desirable response, such as preventing CNS-OT in a subject or preventing seizures in a subject.

A therapeutically effective amount may be administered in one or more administrations (e.g., the composition may be given as a preventative treatment or therapeutically at any stage of disease progression, before or after symptoms, and the like), applications or dosages and is not intended to be limited to a particular formulation, combination or administration route. It is within the scope of the present disclosure that the disclosed ketogenic compound may be administered at various times during the course of treatment of the subject. The times of administration and dosages used will depend on several factors, such as the goal of treatment, condition of the subject, etc. and can be readily determined by one skilled in the art. Administration may be adjusted according to individual need and professional judgment of a person administrating or supervising the administration of the compounds used in the present invention.

"Transesterification" refers to the reaction of an ester with an alcohol to form a new ester compound.

2. Ketogenic Compositions

Disclosed herein are compositions comprising one or more ketogenic compounds. The ketogenic compound may be any compound capable of elevating ketone body concentrations in a subject. For example, the ketogenic compound may elevate expression of βHB following administration to the subject. The ketogenic compound may be a ketone body precursor, a ketone ester, a ketone salt, or a combination thereof. For example, the ketogenic compound may be a ketone body precursor or derivative thereof. Any suitable ketone body precursor which will be metabolized into a ketone body upon administration to the subject may be used. For example, the ketogenic compound may be 1,3-butanediol, acetoacetate, or βHB moieties or derivatives thereof, including esters and salts thereof. For example, the ketogenic compound may be 1,3-butanediol-acetoacetate diester. The ketogenic compound may be sodium-3-hydroxybutyrate. The ketogenic compound may be R,S-sodium-3-hydroxybutyrate.

The ketogenic compound may be a ketone ester. Any suitable ketone ester may be used in the disclosed ketogenic compositions. Ketone esters may be prepared using any suitable physiologically compatible alcohol. Examples of polyhydric alcohols suitable for preparing such esters include carbohydrates and carbohydrate derivatives, such as carbohydrate alcohols. Examples of carbohydrates include, without limitation, altrose, arabinose, dextrose, erythrose, fructose, galactose, glucose, gulose, idose, lactose, lyxose, mannose, ribose, sucrose, talose, threose, xylose and the like. The ketone ester may be a monoester. The ketone ester may be a diester, The ketone ester may be a polyester. For example, the ketone ester may be 1,3-butanediol-acetoacetate monoester. The ketone ester may be 1,3-butanediol-acetoacetate diester.

The ketogenic compound may be a ketone salt. The ketone salt may be combined with a monovalent cation, divalent cation, or alkaline amino acid. Any suitable ketone salt may be used. For example, the ketone salt may be a βHB salt. The ketone salt may be a βHB mineral salt. For example, the βHB mineral salt may be potassium βHB, sodium βHB, calcium βHB, magnesium βHB, lithium BHB, or any other feasible non-toxic mineral salts of βHB. The ketone salt may be a βHB organic salt. Organic salts of βHB include salts of organic bases such as arginine lysine βHB, lysine βHB, histidine βHB, ornithine βHB, creatine βHB, agmatine βHB, and citrulline βHB. The ketone salt may be a combination of βHB salts. For example, the ketone salt may be a sodium/potassium βHB mineral salt. The ketone salt may be a sodium/calcium βHB mineral salt ($Na^+Ca^{2+}$ βHB).

The ketone salt may be mixed into a solution. For example, a βHB mineral salt may be mixed into a solution. The βHB mineral salt may be from 1 to 99% of a solution. For example, the βHB mineral salt may be 5-95%, 10-90%, 20-80%, 30-70%, 40-60%, or about 50% of a solution.

The composition may additionally comprise at least one medium chain fatty acid or ester thereof. For example, the composition may additionally comprise at least one medium chain triglyceride. The composition may comprise MCT oil. Sources of the medium chain fatty acid or an ester thereof include coconut oil, coconut milk powder, fractionated coconut oil, palm oil, palm kernel oil, caprylic acid, isolated medium chain fatty acids such as isolated hexanoic acid, isolated octanoic acid, isolated decanoic acid, medium chain triglycerides either purified or in natural form such as coconut oil, and ester derivatives of the medium chain fatty acids ethoxyiated triglyceride, enone triglyceride derivatives, aldehyde triglyceride derivatives, monoglyceride derivatives, diglyceride derivatives, and triglyceride derivatives, and salts of the medium chain triglycerides. Ester derivatives optionally include alkyl ester derivatives, such as methyl, ethyl, propyl, butyl, hexyl, etc. Derivatives may be prepared by any process known in the art, such as direct esterification, rearrangement, fractionation, transesterification, or the like.

The disclosed composition may comprise any combination of one or more ketogenic compounds. For example, the disclosed composition may comprise a combination of any one or more of a ketone ester, a ketone salt, a ketone body precursor, and a medium chain fatty acid. The composition may comprise at least one ketone salt and at least one ketone ester. For example, the composition may comprise sodium/calcium βHB mineral salt and 1,3 butanediol acetoacetate diester. The composition may comprise at least one ketone salt and at least one medium chain fatty acid. For example, the composition may comprise sodium/calcium βHB mineral salt and a MCT. The composition may comprise at least one ketone ester and at least one medium chain fatty acid. For example, the composition may comprise 1,3 butanediol acetoacetate diester and a MCT. The composition may comprise a ketone salt and a MCT mixed at an approximate 1:1 ratio. The composition may comprise a ketone ester and a MCT mixed at an approximate 1:1 ratio. The composition may comprise a ketone precursor and a MCT mixed at an approximate 1:1 ratio. The above combinations are intended strictly to provide examples and are in no way limiting to other combinations that may be used.

The composition may additionally comprise other nutritional substrates. For example, the composition may additionally comprise free amino acids, amino acid metabolites, vitamins, minerals, electrolytes and metabolic optimizers such as NADH, soluble ubiquinol, tetrahydrobiopeterin, alpha-ketoglutaric acid, carnitine, and/or alpha lipoic acid, nutritional co-factors, calcium beta-methyl-beta-hydroxybutyrate, arginine alpha-ketoglutarate, sodium R-alpha lipoic acid, thiamine, riboflavin, niacin, pyridoxine, ascorbic acid, citric acid, malic acid, sodium benzoate, potassium sorbate, acesulfame K, aspartame, xanthan gum, or a combination thereof. Non-limiting examples of nutritional co-factors include R-alpha lipoic acid, acetyl-1-carnitine, ketoisocaproate, alpha-ketoglutarate, alpha-hydroxyisocaproate, creatine, branched chain amino acids (leucine, isoleucine, valine), beta-hydroxy-beta methylbutyrate (HMB), B vitamins, vitamin C, soluble ubiquinol, and carnitine that assist in mitochondrial function.

The ketogenic composition may further comprise a pharmaceutically acceptable carrier or excipient. Such carriers may be sterile liquids, such as water and oils. For example, the carrier may be a petroleum oil such as mineral oil; vegetable oil such as peanut oil, soybean oil, or sesame oil; animal oil; or oil of synthetic origin. Suitable carriers also include ethanol, dimethyl sulfoxide, glycerol, silica, alumina, starch, sorbitol, inosital, xylitol, D-xylose, mannitol, powdered cellulose, microcrystalline cellulose, talc, colloidal silicon dioxide, calcium carbonate, magnesium carbonate, calcium phosphate, calcium aluminium silicate, aluminium hydroxide, sodium starch phosphate, lecithin, and equivalent carriers and diluents. Saline solutions and aqueous dextrose and glycerol solutions can also be employed as liquid carriers. Suitable carriers include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The ketogenic composition may contain minor amounts of wetting or emulsifying agents. The ketogenic composition may contain pH buffering agents.

The ketogenic composition may be in a variety of forms. For example, the ketogenic composition may be in solid form, semi-solid form, or a liquid dosage forms. The ketogenic composition may be in the form of tablets, pills, powders, liquid solutions or suspensions, suppositories, and injectable or infusible solutions. The preferred form depends on the intended mode of administration and therapeutic application.

3. Methods of Treating CNS-OT or Seizures in a Subject

Disclosed herein are methods of treating CNS-OT in a subject. The method may comprise administering a disclosed ketogenic composition to the subject. The composition may prevent CNS-OT in the subject. The composition may prevent tonic-clonic seizures in the subject. The composition may delay the onset of tonic-clonic seizures in the subject. The composition may reduce the severity of tonic-clonic seizures in the subject.

Further disclosed herein are methods of treating seizures in a subject. The method may comprise administering a disclosed ketogenic composition to the subject. The composition may prevent seizures in the subject. The composition may delay the onset of seizures in the subject. The composition may reduce the severity of seizures in the subject. The subject may be diagnosed with a seizure disorder. The seizure disorder may be any condition in which seizures may be a symptom. For example, the subject may be diagnosed with epilepsy.

The composition may be delivered to the subject in any dose sufficient to achieve the desired therapeutic effect. For example, the composition may be administered in a dosage range of 1 mg ketogenic compound/kg of body weight to 100 g ketogenic compound/kg body weight. A therapeutically effective amount of a ketogenic compound of the disclosed composition may be about 1 mg ketogenic compound/kg body weight to about 25,000 mg/kg, about 5 mg/kg to about 10,000 mg/kg, about 10 mg/kg to about 5,000 mg/kg, about 15 mg/kg to about 1,000 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg. A therapeutically effective amount of a ketogenic compound of the disclosed composition may be about 1.25 mg/kg, about 2.5 mg/kg, about 5 mg/kg, or about 10 mg/kg.

The composition may be administered to the subject at any time point appropriate to achieve the desired therapeutic effect. For example, the composition may be administered to the subject prior to potential hyperbaric oxygen exposure. For example, the composition may be administered to the subject at least 30 minutes prior to potential hyperbaric oxygen exposure. For example, the composition may be administered to the subject at least 30 minutes, at least 40 minutes, at least 50 minutes, at least 60 minutes, at least 90 minutes, at least 120 minutes, at least 150 minutes, or at least 180 minutes prior to potential hyperbaric oxygen exposure.

The composition may be administered in various ways, including, for example, orally, intragastricly, or parenterally (referring to intravenously and intra-arterially and other appropriate parenteral routes), among others. Administration may be as a single dose, or multiple doses over a period of time. Administration may be as a single dose, or multiple doses over a period of time. In an embodiment, the composition may be administered chronically, for example, between about 1 day and about 7 days), or sub-chronically (e.g., more than 7 days). For example, multiple doses may be delivered over 1 day, 3 days, 5 days, 7 days, 10 days, 14 days, or more, 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, or more, 1 month, 2 months, 3 months, 4 months, 5 months, 6 months, 7 months, 8 months, 9 months, 10 months, 11 months, 12 months, or more.

The composition may be a solid, for example a powder, tablet, gel, bar, confectionary product, or a granule, and intended for use as a solid oral dose form. The solid composition may be mixed before use with a liquid, such as a water-based liquid (e.g., fruit drink, dairy product, milk, and yogurt), to provide a liquid drink for the user. The composition may be provided, as desired, as a liquid product in a form ready for consumption or as a concentrate or paste suitable for dilution on use. The liquid product may be pH adjusted with citric and/or malic acid, and artificial sweetener and flavoring can be added. The liquid product may be homogenized and pasteurized. The composition may further comprise a pharmaceutically acceptable excipient, diluent, or carrier.

The levels of circulating glucose and ketone bodies may be measured in a subject prior to or following administration of the disclosed composition. Circulating levels may be determined from, for example, bodily fluids (e.g. blood, serum, plasma, or urine) or breath (such as, acetone on the breath). Any suitable measuring device or kit known in the art may be used, such as the PRECISION XTRA® blood glucose and ketone monitoring kit (Abbott Laboratories, Abbott Park, Ill.).

In the methods of use described herein, additional therapies may be administered simultaneously or sequentially with the disclosed compositions. For example, additional therapies for the treatment or prevention of CNS-OT or seizures may be administered to the subject. Sequential administration includes administration before or after the disclosed compositions. In some embodiments, the additional therapeutic agent or agents may be administered in the same composition to the subject. In other embodiments, there may be an interval of time between administration of the additional therapeutic agent and the disclosed compositions. In some embodiments, administration of an additional therapeutic agent with the disclosed compositions may allow lower doses of the other therapeutic agents and/or administration at less frequent intervals. When used in combination with one or more other active ingredients, the compositions of the present invention and the other active ingredients may be used in lower doses than when each is used singly.

The invention further discloses a kit, which may be used to treat CNS-OT or seizures in a subject. For example, the kit may be used to prevent or delay CNS-OT or seizures in a subject. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The compositions and methods of the invention will be better understood by reference to the following examples, which are intended as an illustration of and not a limitation upon the scope of the invention.

4. Examples

Example 1

Ketogenic Compositions Increase Latency to Seizure and Reduce Seizure Severity in Rats The effect of various ketogenic compositions on latency to seizure and seizure severity was tested in a rat model of CNS-OT. Adult male Sprague-Dawley rats (n=60), 250-300 grams (Harlan) were used in the experiments described herein. Rats were given normal chow and water ad libitum and kept on a 12-hour light/dark cycle. At 16 months, the rats were assigned to one of 5 treatment groups: control (water), 1,3-butanediol acetoacetate diester (KE, 10 g/kg), KE/2 (KE, 5 g/kg), KE+MCT (1,3-butanediol acetoacetate diester+medium chain triglyceride, 5 g/kg+5 g/kg) and KS+MCT ($Na^+Ca^{2+}BHB$ 5 g/kg+MCT 5 g/kg). Rats received one dose of the designated ketogenic agent or water by oral gavage. Rats were then placed into the hyperbaric chamber 29-30 minutes after treatment, and pressurized to 5 atmospheres as provided below, such that rats were exposed to the hyperbaric conditions at 60 minutes after treatment.

The hyperbaric system consisted of two main elements: 1) a plexiglass chamber (~3 liter capacity, Diamond Box, Buxco, Electronics Inc., model PLY3114), that housed the rat during the experiment, and 2) a hyperbaric chamber (Reimers System Inc.—7.8 ATA MWP), that contained the plexiglass chamber and functioned as the pressure vessel. Both chambers were connected to an air compressor (oil-less rotary scroll compressor—model DK6086, Powerex).

Rats were placed in the hyperbaric chamber, where the rats were allowed 10 minutes to acclimate in air. Then the plexiglass chamber was filled with pure oxygen, and the rats were allowed another 15 minutes to acclimate. The outer chamber was pressurized using air (capacity ~205 liters) to minimize the risk of an electrical-induced fire. Next, both chambers were compressed to 5 atmospheres absolute (ATA) at a rate of approximately 1 ATA/min. Each experiment was visually monitored via a live camera.

Rats remained at 5 ATA until exhibiting CNS-OT seizures, defined by tonic-clonic movements. Tonic-clonic movements were defined when exhibiting two or more of the following symptoms: head bobbing up and down; blinking; one or two front paws elevated, most often with opened toes; pushing the ground with 2 front paws for at least 10 sec; multiple and intense wet-dog shakes; or trashing around. Experiments were immediately terminated if rats exhibited signs of pulmonary oxygen toxicity (observed as gasping and/or difficulty breathing) or after a maximum of 120 minutes at 5 ATA.

Latency to seizure (LS) was calculated from the moment at which the internal and the external chambers reached 5 ATA until the onset of CNS-OT seizures, as identified above. After the onset of seizures, the plexiglass chamber was flushed with air to quickly terminate seizure, and both chambers decompressed to sea level. Decompression rate was 1 ATA/min. A small sample of blood was drawn and tested immediately for glucose and beta-hydroxybutyrate levels.

The use of 10 g/kg 1,3-butanediol acetoacetate diester and the combination of 5 g/kg 1,3-butanediol acetoacetate diester with 5 g/kg medium chain triglycerides (pharmaceutical grade formulation of caprylic acid and capric acid; NOW Foods, Bloomingdale, Ill.) increased time to latency by about 3× compared to control, as seen in FIG. 1. Reducing the dosage of 1,3-butanediol acetoacetate diester from 10 g/kg to 5 g/kg lessened the effects of treatment such that latency was about 2× compared to control. Treatment with 5 g/kg $Na^+Ca^{2+}$BHB with 5 g/kg medium chain triglycerides showed about the same level of latency as the control. As shown in Table 1, treatment with 1,3-butanediol acetoacetate diester with 5 g/kg medium chain triglycerides was the only treatment that significantly altered latency to seizure compared to control when all animals (including outliers) were considered.

TABLE 1

Statistical analysis of results showing latency to time of seizure for all collected data

| Group | Control | KE | KE + MCT | KE/2 | KS + MCT | KE/ KE + MCT |
|---|---|---|---|---|---|---|
| N# | 9 | 9 | 9 | 8 | 7 | |
| T-test (p) | | 0.079† | 0.049* | 0.256† | 0.909† | 0.985† |

*p < 0.05
†not significant

Figure 2:
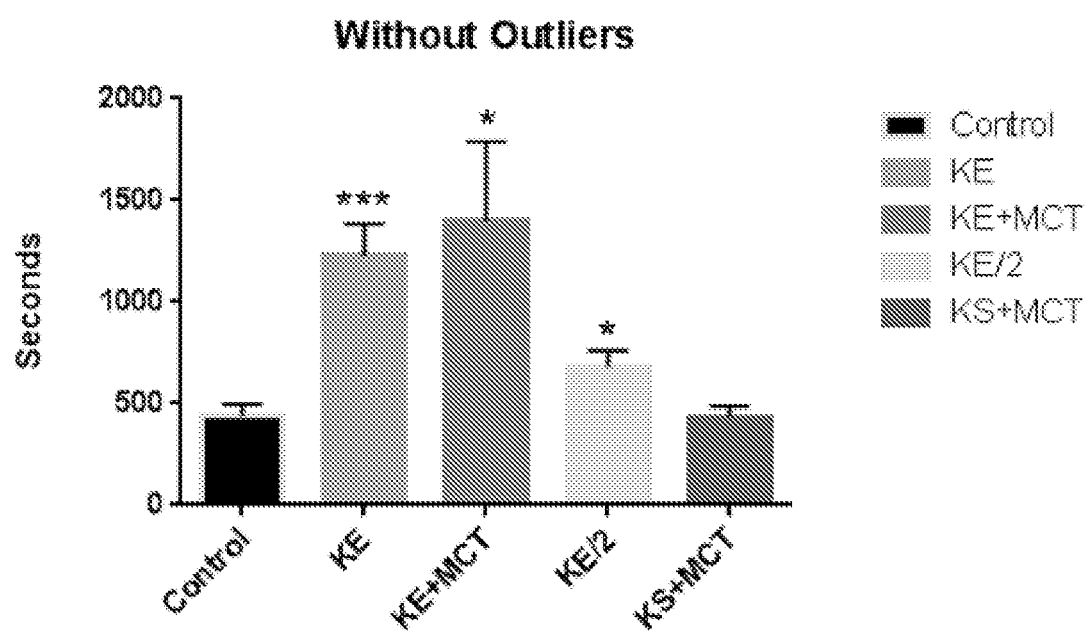

The data collected above was adjusted for outliers by removing results outside of 2 standard deviations from the mean. As seen in FIG. 2 and Table 2, treatment with 10 g/kg 1,3-butanediol acetoacetate diester significantly increased latency to seizure compared to control. Treatment with 5 g/kg 1,3-butanediol acetoacetate diester with 5 g/kg medium chain triglycerides similarly increased latency to seizure, with LS times around or above 3× the control times. Treatment with 5 g/kg 1,3-butanediol acetoacetate diester also significantly increased latency to seizure compared to control. Analysis of the data show the majority of treatments significantly differed from the control, as seen in Table 2.

Figure 3:
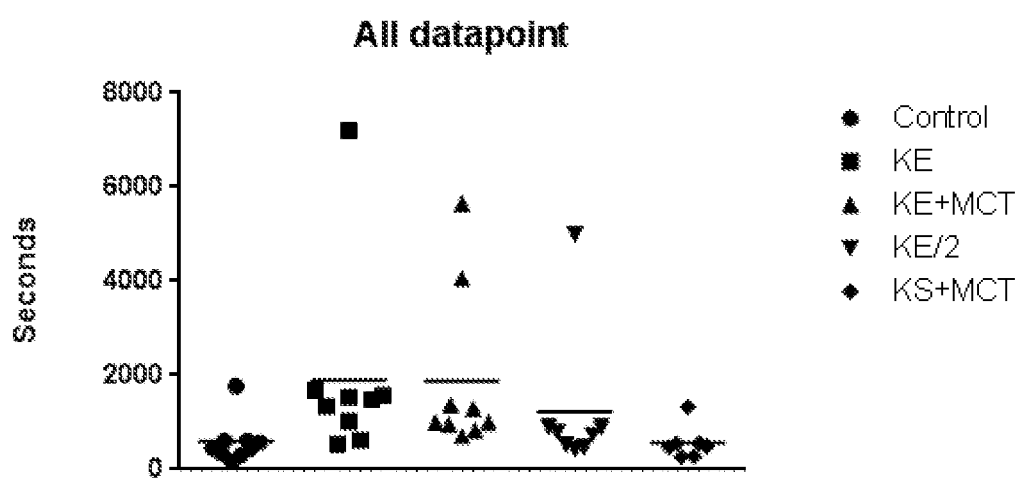

Plotting the individual results, as seen in FIG. 3, shows a strong clustering of data with strong outliers for both 1,3-butanediol acetoacetate diester treatments and the 1,3-butanediol acetoacetate diester with medium chain triglyceride treatment.

Figure 4:
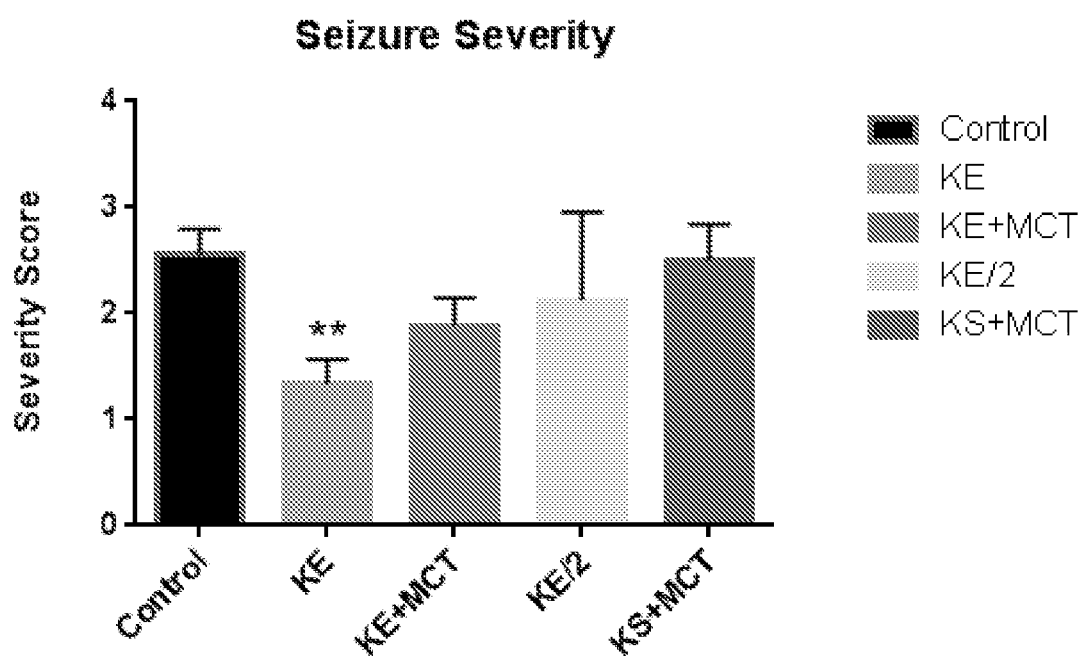
FIG. 4 shows seizure severity upon CNS toxicity for all tested rats broken down by treatment regimen.

An analysis of all rats showed the degree of seizure severity correlated to the time-to-seizure (latency), as seen in FIG. 4. Scoring for seizure severity was as follows;

0: no tonic clonic seizure was observed.

1: animal shows symptoms to fulfill endpoint criteria but symptoms are very subtle, seizure does not last long and animal does not seem exhausted after seizure.

2: animal shows intense seizure for less than 10 seconds or subtle symptoms for more than 10 seconds.

3: animal shows violent seizure that results in intense, jerky movements, thrashing around, seizure last longer than 10 seconds and animal seems to be exhausted for long period of time after seizure.

Treatment with 10 g/kg 1,3-butanediol acetoacetate diester showed the strongest suppression of seizure severity (p=0.0023). The combination of 5 g/kg 1,3-butanediol acetoacetate diester with 5 g/kg medium chain triglycerides and 5 g/kg 1,3-butanediol acetoacetate diester both showed some suppression, though 5 g/kg 1,3-butanediol acetoacetate diester possesses significant overlap with the control. Treatment with 5 g/kg $Na^+Ca^{2+}$BHB and 5 g/kg medium chain triglycerides exhibited similar severity to control rats.

Figure 5:
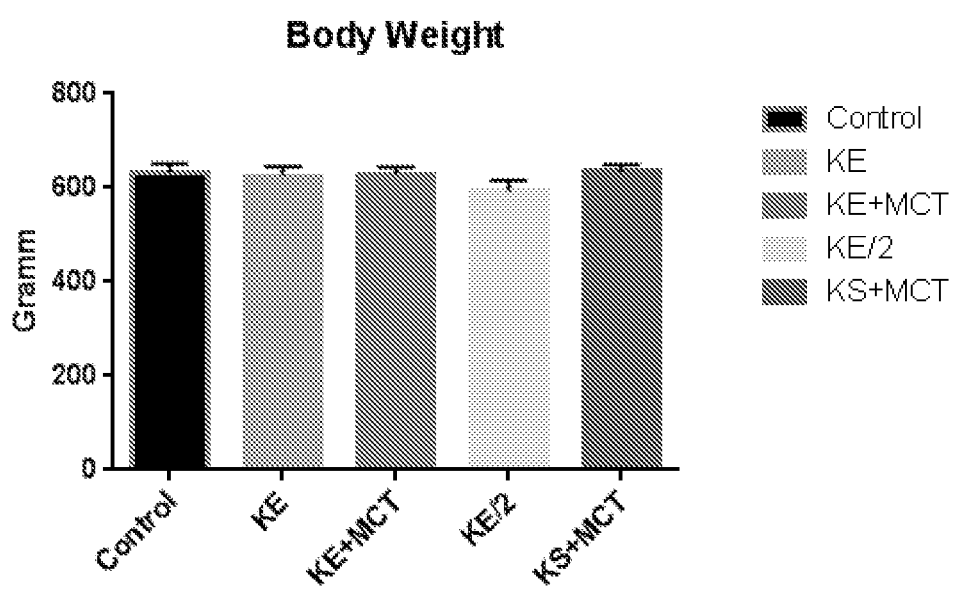
FIG. 5 shows body weight for all tested rats broken down by treatment regimen that was measured immediately before the oral gavage.
Figure 6:
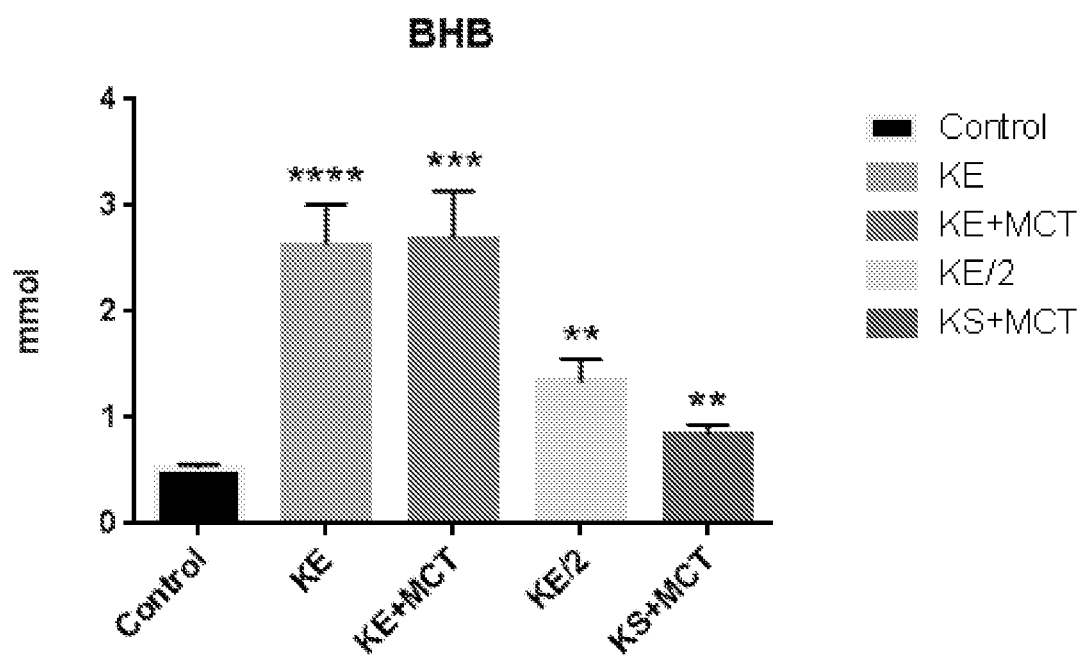
FIG. 6 shows blood β-hydroxybutyrate levels for all tested rats broken down by treatment regimen. Blood β-hydroxybutyrate levels were measured immediately after decompressing the chamber and removing the rat from the chamber.

Body weights were collected for all rats prior to oral gavage of treatment. Body weights before treatment are shown in FIG. 5. Blood concentrations of glucose and beta-hydroxybutyrate (BHB) were determined utilizing a commercially available glucose/ketone monitoring system (Precision Xtra® blood glucose and ketone meter) immediately following removal from the hyperbaric chamber. Treatment with 10 g/kg 1,3-butanediol acetoacetate diester and the combination of 5 g/kg 1,3-butanediol acetoacetate diester with 5 g/kg medium chain triglycerides increased BHB levels by about 5×-6× compared to control, as seen in FIG. 6. Reducing the dosage of 1,3-butanediol acetoacetate diester to 5 g/kg resulted in levels of BHB that were about 3× compared to control. Treatment with 5 g/kg $Na^+Ca^{2+}$BHB with 5 g/kg medium chain triglycerides increased BHB levels about 2× over the control. Thus, the level of BHB correlated to the latency to seizure. Analysis indicated that all treatment types demonstrated significant elevations in BHB levels compared to control, as seen in Table 3.

TABLE 2

Statistical analysis of results showing latency to time of seizure with exclusion of outliers using 2 standard deviations as the cut off

| Group | Control | KE | KE + MCT | KE/2 | KS + MCT | KE/KE + MCT | KE/KE/2 |
|---|---|---|---|---|---|---|---|
| N# | 8 | 8 | 8 | 7 | 6 | | |
| T-test (p) | | 0.0003*** | 0.028* | 0.023* | 0.951† | 0.685† | 0.01* |

*p < 0.05
***p < 0.0005
†not significant

TABLE 3

Statistical analysis of results showing BHB levels for all collected data

| Group | Control | KE | KE + MCT | KE/2 | KS + MCT |
|---|---|---|---|---|---|
| N# | 9 | 9 | 9 | 8 | 7 |
| T-test (p) | | <0.0001*** | 0.002** | 0.0012** | 0.0024** |

**p < 0.005
***p < 0.0005

Figure 7:
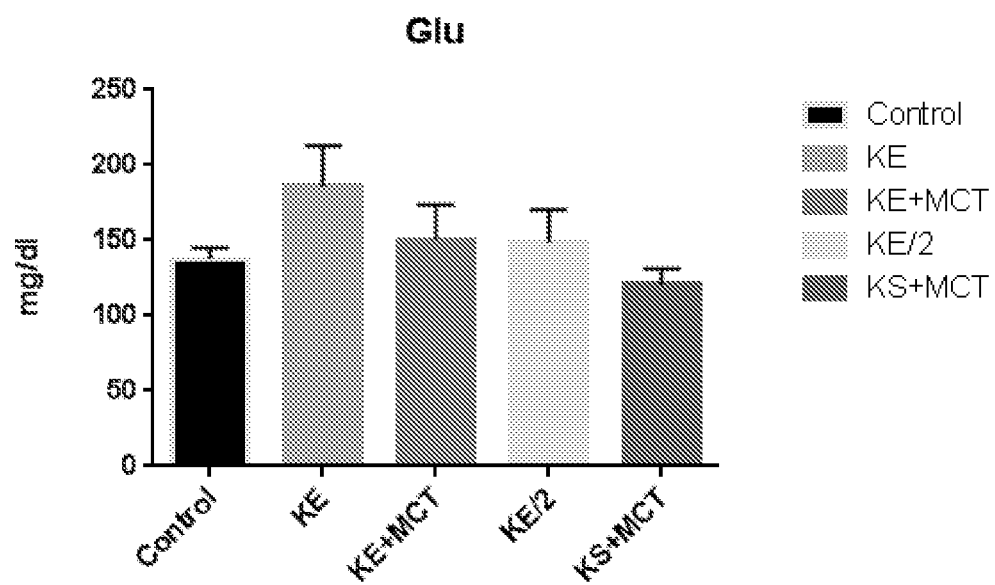
FIG. 7 shows blood glucose levels for all tested rats broken down by treatment regimen. Blood glucose levels were measured immediately after decompressing the chamber and removing the rat from the chamber.

Blood glucose levels were also measured. As seen in FIG. 7, rats treated with 10 g/kg 1,3-butanediol acetoacetate diester showed the highest blood glucose levels. Rats treated with 5 g/kg 1,3-butanediol acetoacetate diester with 5 g/kg medium chain triglycerides and 5 g/kg 1,3-butanediol acetoacetate diester showed similar glucose levels, suggesting that the amount of 1,3-butanediol acetoacetate diester correlates with glucose levels. Rats treated with 5 g/kg $Na^+Ca^{2+}BHB$ with 5 g/kg medium chain triglycerides showed the lowest level of blood glucose, even lower than that seen in control rats.

The relationship between seizure latency and blood βHB levels was analyzed using a Pearson product-moment correlation coefficient. The correlation results are shown in Table 4 for all data samples. Control rats and rats treated with 5 g/kg 1,3-butanediol acetoacetate diester with 5 g/kg medium chain triglycerides show an inverse relationship between the latency-to-seizure time and blood βHB levels. Rats treated with 10 g/kg 1,3-butanediol acetoacetate or 5 g/kg 1,3-butanediol acetoacetate also showed a very small, inverse correlation. By comparison, rats treated with 5 g/kg $Na^+Ca^{2+}$ βHB with 5 g/kg medium chain triglycerides exhibited very little correlation between latency to seizure time and blood βHB levels.

TABLE 4

Correlation of latency to seizure-BHB for all collected data

| Group | Control | KE | KE + MCT | KE/2 | KS + MCT |
|---|---|---|---|---|---|
| | −0.381 | −0.06 | −0.33 | −0.099 | 0.009 |

When the outliers were removed, only the control exhibited an inverse relationship between the time-to-seizure and levels of βHB. By comparison, the remaining treatments all exhibited a positive correlation between the time-to-seizure and levels of BHB found in the blood, as seen in Table 5.

TABLE 5

Correlation of latency to seizure-BHB after closing out the outliers using 2 standard deviations

| Group | Control | KE | KE + MCT | KE/2 | KS + MCT |
|---|---|---|---|---|---|
| | −0.649 | 0.71 | 0.532 | 0.307 | 0.387 |

For reasons of completeness, various aspects of the invention are set out in the following numbered clauses:

Clause 1: A method of treating central nervous system oxygen toxicity (CNS-OT) in a subject, the method comprising administering a composition comprising a therapeutically effective amount of one or more ketogenic compounds to the subject.

Clause 2: The method of clause 1, wherein the composition prevents CNS-OT in the subject.

Clause 3: The method of clause 1, wherein the composition prevents tonic-clonic seizures in the subject.

Clause 4: The method of clause 1, wherein the composition delays the onset of tonic-clonic seizures in the subject.

Clause 5: The method of clause 1, wherein the composition reduces the severity of tonic-clonic seizures in the subject.

Clause 6: The method of clause 1, wherein the composition comprises one or more ketogenic compounds selected from the group consisting of a ketone ester, a ketone salt, a ketone body precursor, and a combination thereof.

Clause 7: The method of clause 6, wherein the one or more ketogenic compounds is a ketone ester.

Clause 8: The method of clause 7, wherein the ketone ester is 1,3-butanediol-acetoacetate diester.

Clause 9: The method of clause 7, wherein the composition further comprises a medium chain triglyceride.

Clause 10: The method of clause 9, wherein the ketone ester and the medium chain triglyceride have an approximate 1:1 ratio.

Clause 11: The method of clause 6, wherein the one or more ketogenic compounds is a ketone salt.

Clause 12: The method of clause 11, wherein the ketone salt is a β-hydroxybutyrate salt.

Clause 13: The method of clause 12, wherein the ketone salt is a β-hydroxybutyrate mineral salt.

Clause 14: The method of clause 13, wherein the β-hydroxybutyrate mineral salt is a $Na^+Ca^{2+}$ β-hydroxybutyrate mineral salt.

Clause 15: The method of clause 11, wherein the composition further comprises a medium chain triglyceride.

Clause 16: The method of clause 15, wherein the ketone salt and the medium chain triglyceride have an approximate 1:1 ratio.

Clause 17: A method of treating seizures in a subject, the method comprising administering a composition comprising a therapeutically effective amount of one or more ketogenic compounds to the subject.

Clause 18: The method of clause 17, wherein the composition prevents seizures in the subject.

Clause 19: The method of clause 17, wherein the composition delays the onset of seizures in the in the subject.

Clause 20: The method of clause 17, wherein the composition reduces the severity of seizures in the subject.

Clause 21: The method of clause 17, wherein the subject is diagnosed with a seizure disorder.

Clause 22: The method of clause 21, wherein the seizure disorder is epilepsy.

Clause 23: The method of clause 17, wherein the composition comprises one or more ketogenic compounds selected from the group consisting of a ketone ester, a ketone salt, a ketone body precursor, and a combination thereof.

Clause 24: The method of clause 23, wherein the one or more ketogenic compounds is a ketone ester.

Clause 25: The method of clause 24, wherein the ketone ester is 1,3-butanediol-acetoacetate diester.

Clause 26: The method of clause 24, wherein the composition further comprises a medium chain triglyceride.

Clause 27: The method of clause 26, wherein the ketone ester and the medium chain triglyceride have an approximate 1:1 ratio.

Clause 28: The method of clause 23, wherein the one or more ketogenic compounds is a ketone salt.

Clause 29: The method of clause 28, wherein the ketone salt is a β-hydroxybutyrate salt.

Clause 30: The method of clause 29, wherein the ketone salt is a β-hydroxybutyrate mineral salt.

Clause 31: The method of clause 30, wherein the β-hydroxybutyrate mineral salt is a Na⁺Ca²⁺ β-hydroxybutyrate mineral salt.

Clause 32: The method of clause 28, wherein the composition further comprises a medium chain triglyceride.

Clause 33: The method of clause 32, wherein the ketone salt and the medium chain triglyceride have an approximate 1:1 ratio.

Clause 34: The method of clause 1 or clause 17, wherein the composition is administered orally.

Clause 35: The method of clause 1 or clause 17, wherein the subject is a mammal.

Clause 36: The method of clause 35, wherein the subject is κ human.

What is claimed is:

1. A method of treating or preventing central nervous system oxygen toxicity (CNS-OT) in a subject in need thereof, the method comprising administering a composition comprising a therapeutically effective amount of a ketone ester and a medium chain triglyceride to the subject, wherein administering the composition comprises administering a daily amount of about 1 mg/kg to about 5 g/kg bodyweight of each of the ketone ester and MCT.

2. The method of claim 1, wherein the composition prevents, delays the onset of, or reduces the severity of tonic-clonic seizures in the subject.

3. The method of claim 1, wherein the ketone ester is 1,3-butanediol-acetoacetate diester.

4. The method of claim 1, wherein the ketone ester and the medium chain triglyceride have an approximate 1:1 ratio.

5. The method of claim 1, wherein the composition further comprises a ketone salt.

6. The method of claim 5, wherein the ketone salt is a β-hydroxybutyrate salt.

7. The method of claim 6, wherein the ketone salt is a β-hydroxybutyrate mineral salt.

8. The method of claim 7, wherein the β-hydroxybutyrate mineral salt is a Na⁺Ca²⁺ β-hydroxybutyrate mineral salt.

9. The method of claim 8, wherein the ketone salt and the medium chain triglyceride have an approximate 1:1 ratio.

10. A method of treating or preventing seizures in a subject in need thereof, the method comprising administering a composition comprising a therapeutically effective amount of a ketone ester and a medium chain triglyceride to the subject,
    where in administering the composition comprises administering a daily amount of about 1 mg/kg to about 5 g/kg bodyweight of each of the ketone ester and MCT.

11. The method of claim 10, wherein the composition delays the onset of or reduces the severity of seizures in the subject.

12. The method of claim 10, wherein the seizure is from epilepsy.

13. The method of claim 10, wherein the ketone ester is 1,3-butanediol-acetoacetate diester.

14. The method of claim 10, wherein the ketone ester and the medium chain triglyceride have an approximate 1:1 ratio.

15. The method of claim 10, wherein the composition further comprises one or more ketogenic compounds is a ketone salt.

16. The method of claim 15, wherein the ketone salt is κ β-hydroxybutyrate salt.

17. The method of claim 16, wherein the ketone salt is a β-hydroxybutyrate mineral salt.

18. The method of claim 17, wherein the β-hydroxybutyrate mineral salt is a Na⁺Ca²⁺ β-hydroxybutyrate mineral salt.

19. The method of claim 15, wherein the ketone salt and the medium chain triglyceride have an approximate 1:1 ratio.

20. A method of treating or preventing epileptic seizures in a subject in need thereof, the method comprising administering a composition comprising a therapeutically effective amount of a ketone supplement comprising a ketone ester to the subject.

* * * * *